(12) United States Patent
Lin et al.

(10) Patent No.: US 11,694,887 B2
(45) Date of Patent: Jul. 4, 2023

(54) MASS SPECTROMETER, MASS SPECTROMETRY METHOD AND DETECTION SYSTEM

(71) Applicant: Shimadzu Corporation, Kyoto (JP)

(72) Inventors: Yiming Lin, Shanghai (CN); Wenjian Sun, Shanghai (CN)

(73) Assignee: SHIMADZU CORPORATION, Kyoto (JP)

(*) Notice: Subject to any disclaimer, the term of this patent is extended or adjusted under 35 U.S.C. 154(b) by 0 days.

(21) Appl. No.: 17/321,658

(22) Filed: May 17, 2021

(65) Prior Publication Data

US 2021/0366700 A1 Nov. 25, 2021

(30) Foreign Application Priority Data

May 21, 2020 (CN) .......................... 202010437734.1

(51) Int. Cl.
*H01J 49/24* (2006.01)
*H01J 49/00* (2006.01)
*G01N 30/72* (2006.01)
*H01J 49/26* (2006.01)
*G01N 33/00* (2006.01)
*G01N 30/02* (2006.01)

(52) U.S. Cl.
CPC .......... *H01J 49/24* (2013.01); *G01N 30/7206* (2013.01); *G01N 33/0047* (2013.01);
(Continued)

(58) Field of Classification Search
CPC ........ H01J 49/24; H01J 49/0031; H01J 49/26; H01J 49/422; H01J 49/0013;
(Continued)

(56) References Cited

U.S. PATENT DOCUMENTS 5,313,061 A * 5/1994 Drew ...................... H01J 49/26
250/296
8,487,248 B2 * 7/2013 Green ................. H01J 49/4235
250/290
(Continued)

FOREIGN PATENT DOCUMENTS

CN 109142639 A * 1/2019

OTHER PUBLICATIONS

Peihe Jiang et al., "Low-vacuum cylindrical ion trap mass spectrometry", Instrumentation Science & Technology, 2018.
(Continued)

*Primary Examiner* — Michael Maskell
(74) *Attorney, Agent, or Firm* — Locke Lord LLP; Tim Tingkang Xia, Esq.

(57) ABSTRACT

The invention relates to a mass spectrometer, a mass spectrometry method and a detection system. The mass spectrometer includes a vacuum chamber having a working pressure being 0.1 Pa≤P≤10 Pa; a linear ion trap, arranged in the vacuum chamber, wherein a field radius r of the linear ion trap is r≤5 mm; and a power supply, configured to provide a radio-frequency voltage for the linear ion trap, a frequency f of the radio-frequency voltage being 2 MHz≤f≤10 MHz. Because a vacuum level is relatively low, this vacuum condition may be realized by selecting a roughing pump for evacuating; and compared with a combined pump unit which is generally selected by a traditional mass spectrometer using the linear ion trap and is composed of a turbo molecular pump and a roughing pump, the roughing pump has a lower pumping speed, smaller size and lower manufacturing cost.

12 Claims, 7 Drawing Sheets

(52) U.S. Cl.
CPC .......... *H01J 49/0031* (2013.01); *H01J 49/26* (2013.01); *G01N 2030/025* (2013.01)

(58) Field of Classification Search
CPC ............ H01J 49/4225; G01N 30/7206; G01N 33/0047; G01N 2030/025; G01N 27/62; G01N 30/02; G01N 30/72
USPC .................... 250/281, 282, 290, 292, 293
See application file for complete search history.

(56) References Cited

U.S. PATENT DOCUMENTS

| | | | |
|---|---|---|---|
| 8,525,111 B1 | 9/2013 | Brown et al. | |
| 9,184,039 B2* | 11/2015 | Pringle | H01J 49/062 |
| 10,763,098 B2* | 9/2020 | Jiang | H01J 49/0027 |
| 2009/0072136 A1* | 3/2009 | Pringle | H01J 49/4235 |
| | | | 250/290 |
| 2016/0118238 A1* | 4/2016 | Gordon | H01J 49/062 |
| | | | 250/282 |
| 2019/0080895 A1* | 3/2019 | Jiang | H01J 49/403 |

OTHER PUBLICATIONS

Kenion H. Blakeman et al., "High Pressure Mass Spectrometry: The Generation of Mass Spectra at Operating Pressures Exceeding 1 Torr in a Microscale Cylindrical Ion Trap", Analytical Chemistry, 2016.

Chenyue Hou et al., "Towards High Pressure Miniature Protein Mass Spectrometer: Theory and Initial Results", Journal of Mass Spectrometry, 2019, 11, pp. 1621-1632.

* cited by examiner

MASS SPECTROMETER, MASS SPECTROMETRY METHOD AND DETECTION SYSTEM

CROSS-REFERENCE TO RELATED PATENT APPLICATION

This application claims priority to and the benefit of Chinese Patent Application Serial No. 202010437734.1, filed May 21, 2020, which is incorporated herein in its entirety by reference.

TECHNICAL FIELD

The present invention relates to the technical field of mass spectrometers, in particular to a mass spectrometer, a mass spectrometry method and a detection system.

BACKGROUND

Miniaturization is one of main trends in the development of a mass spectrometer, and miniaturization of the mass spectrometer is a systematic project, which is severely restricted by performance requirements, machining difficulty of various components, etc.

For example, because a pump system accounts for a high proportion of the mass spectrometer in weight and size, miniaturization of the pump system is one of important directions of miniaturization development, and miniaturization of the pump system is restricted by the performance requirements of other components as well. Generally speaking, if the size or the weight of the pump system is reduced, a vacuum performance which can be provided by the pump system will also be degraded. However, many components in a mass spectrometer system have certain requirements for the vacuum performance. If the vacuum performance provided by the pump system may not meet the vacuum level requirements of these components (e.g., a mass analyzer), the analytical performance of the mass spectrometer will be caused to be degraded, and even it becomes difficult for the mass spectrometer to meet the requirements (e.g., resolution of the mass analyzer cannot meet the requirement that a full width at half maximum is less than or equal to 1 Th).

In the prior art, in order to meet the requirement of the resolution that the full width at half maximum is less than or equal to 1 Th in a relatively wide mass-to-charge ratio range, such as a mass-to-charge ratio range of 20-600 Th, the mass analyzer needs to work in a vacuum environment of less than 0.1 Pa, thus putting forward a relatively high requirement for the vacuum performance of the pump system. Therefore, the pump system usually needs to be composed of a turbo molecular pump and a roughing pump. The pump system is large in total size and relatively heavy in weight, which not only makes miniaturization of a device difficult, but also makes a manufacturing cost of the mass spectrometer high.

U.S. Pat. No. 8,525,111B1 has disclosed a mass spectrometry system, which includes an ion source, an ion trap and a detector, and two or more of the ion source, the ion trap and the detector are arranged in an air pressure environment of 13.3 Pa-1 atm. In this pressure range, it is difficult for the mass spectrometer to use a detector that depends on a high voltage, such as an electron multiplier/dynode. However, gain cannot be generated when a Faraday cup is used for detecting charges, a high gain amplifier is required, thus the bandwidth and scan speed is limited. On the other hand, the spectrum generated has relatively poor quality of low resolution and signal-to-noise ratio, which affect the qualitative and quantitative analysis.

As disclosed by Jiang et al. in "Low-vacuum cylindrical ion trap mass spectrometry" (*Instrumentation Science & Technology*, 2018), a full width at half maximum FWHM≈2 can be achieved at an air pressure of 2 Pa by employing a cylindrical ion trap (CIT) and using a radio-frequency power supply frequency of 2.4 MHz. If a radio-frequency voltage with a higher frequency is applied, electric discharge may be generated, which hinders further improvement of the resolution.

For example, as disclosed by Blakeman et al. in "High Pressure Mass Spectrometry: The Generation of Mass Spectra at Operating Pressures Exceeding 1 Torr in a Microscale Cylindrical Ion Trap" (*Analytical Chemistry*, 2016), FWHM≤1 Th can be achieved by employing a cylindrical ion trap, at a higher radio-frequency power supply frequency (6-9.5 MHz) and at a very high air pressure (160 Pa). However, the storage capacity of cylindrical ion trap is relatively weak, which affects the dynamic range of mass spectrometry. Moreover, a field radius of the CIT used as mass analyzer is only 0.5 mm, which further reduces the dynamic range. In addition, at such high radio-frequency frequency, in order to avoid discharge, a measurable high end of mass range is greatly reduced.

As disclosed by Xu et al. in "Towards High Pressure Miniature Protein Mass Spectrometer: Theory and Initial Results" (*Journal of Mass Spectrometry*, 2019), a linear ion trap (LIT) is used and is less affected by space charge than a cylindrical ion trap, but resolution is relatively low. A full width at half maximum of the linear ion trap is FWHM≥1.5 Th even at a relatively low air pressure (1.3 Pa).

SUMMARY

In order to solve the above technical problems, the present invention aims to provide a mass spectrometer whose mass analyzer may stably operate under a low vacuum condition, and quality analysis may still be kept at a relatively high level of resolution, for example, a full width at half maximum less than or equal to 1 Th, in a relatively wide mass-to-charge ratio range, for example, in the range of 20-600 Th.

The mass spectrometer includes a vacuum chamber, a range of a working air pressure P of the vacuum chamber being $0.1\ Pa \leq P \leq 10\ Pa$; a linear ion trap, arranged in the vacuum chamber, wherein a field radius r of the linear ion trap is $r \leq 5$ mm; and a power supply, configured to provide a radio-frequency voltage for the linear ion trap, a frequency f of the radio-frequency voltage being $2\ MHz \leq f \leq 10\ MHz$.

In the above technical solution, because the linear ion trap serving as a mass analyzer is set at $0.1\ Pa \leq P \leq 10\ Pa$, and the mass analyzer is basically the apparatus with the highest requirement for a vacuum performance in the mass spectrometer. Generally speaking, it only requires a minimum air pressure required by the mass spectrometer to be in a range of $0.1\ Pa \leq P \leq 10\ Pa$, and then a vacuum level requirement of the mass spectrometer may be met by using a pump with a relatively small size and a relatively low pumping speed, which facilitates miniaturization of the mass spectrometer. Moreover, sensitivity of the linear ion trap working in this pressure range may be improved correspondingly because of better cooling of ions. The efficiencies of ion injection and ejection are improved.

On the other hand, during the process of creating present invention, the inventor found that by limiting the field radius and a voltage frequency of the linear ion trap to the above numerical ranges, the linear ion trap may still obtain a relatively high resolution level even if it works within the pressure range of 0.1 Pa≤P≤10 Pa. For example, it may achieve the resolution level with a full width at half maximum less than or equal to 1 Th in the mass range of 20-600 Th.

If the working pressure P of the vacuum chamber is too low, for example, lower than 0.1 Pa, it will be difficult to achieve by using a small vacuum pump with a relatively low pumping speed, which is not conducive to miniaturization of the mass spectrometer. If the working pressure of the vacuum chamber is too high, for example, higher than 10 Pa, it is prone to cause electric discharge of the detector and the ion trap.

The frequency f of the radio-frequency voltage should not be too high or too low. When the frequency f is too low, for example, when the frequency f is less than 2 MHz, the resolution and the sensitivity of the mass spectrometer are seriously degraded. However, when the frequency f is too high, for example, when the frequency f is greater than 10 MHz, it is not only more difficult to manufacture the power supply, but also prone to cause electric discharge and sample dissociation.

The field radius r should not be too large. For example, when the field radius r is greater than 5 mm, if a voltage with a relatively high frequency is applied to electrodes of the linear ion trap, electric discharge may be caused easily and it is hard to improve the resolution.

In this way, the mass spectrometer provided by the present invention may balance various factors such as miniaturization, machining difficulty, the resolution, the sensitivity and stability, and the mass spectrometer whose mass analyzer may stably operate under a low vacuum condition (for example, 0.1 Pa≤P≤10 Pa), and quality analysis may still be kept at a relatively high level of resolution, for example, the full width at half maximum is less than or equal to 1 Th, in a relatively wide mass-to-charge ratio range, for example, in the range of 20-600 Th.

In a preferred technical solution of the present invention, the mass spectrometer further includes vacuum pump which is connected to the vacuum chamber, wherein the vacuum pump is a reciprocating vacuum pump, a rotary-vane vacuum pump, a piston vacuum pump, a dry scroll pump, a diaphragm vacuum pump or a Roots pump.

According to the preferred technical solution, since the mass analyzer may stably operate under a low vacuum condition (for example, 0.1 Pa≤P≤10 Pa), a vacuum level requirement of the mass spectrometer may be met by using the above type of roughing pump whose ultimate vacuum level is within a range of 0.1 Pa≤P≤10 Pa, and the above type of vacuum pump is more suitable for miniaturization, thus facilitating miniaturization of the mass spectrometer.

In the preferred technical solution of the present invention, a pumping speed S of the vacuum pump is S≤100 L/min.

According to the preferred technical solution, since the mass analyzer may stably operate under a low vacuum condition (for example, 0.1 Pa≤P≤10 Pa), the vacuum level requirement of the mass spectrometer may be met by using a roughing pump which operates at a low pumping speed, and the roughing pump with a low pumping speed is more suitable for miniaturization, thus facilitating miniaturization of the mass spectrometer.

In a preferred technical solution of the present invention, the mass spectrometer further includes a capillary which is configured to guide a sample into the vacuum chamber.

The capillary may be used for introducing neutral samples or ions. In some technical solutions, the capillary is used as an atmospheric pressure interface. In these technical solutions, an inner diameter of the capillary may be set relatively small, less than 100 μm preferably, such that a low vacuum condition of 0.1 Pa≤P≤10 Pa may be realized by using a small vacuum pump with a relatively low pumping speed. In some other technical solutions, the mass spectrometer may also be used in combination with a chromatograph, for example, the capillary may be configured as a capillary chromatographic column of a gas chromatograph.

In a preferred technical solution of the present invention, the mass spectrometer further includes a membrane interface which communicates with the vacuum chamber.

According to the preferred technical solution, the mass spectrometer provided with a membrane interface may be conveniently used in combination with a volatile organic compound (VOC) detection apparatus. In addition, a mass spectrometer provided is a miniaturized mass spectrometer, which may be integrated in the VOC detection apparatus, for example, inside a case of an online monitoring device, so as to improve accuracy of VOC detection.

According to the preferred technical solution, the mass spectrometer further includes a detector which is arranged at an ion outlet of the linear ion trap.

According to the preferred technical solution, an ion signal with relatively high resolution may be collected by arranging the detector near the ion outlet of the linear ion trap. Therefore, by integrating the linear ion trap and the detector in the same vacuum chamber, internal space of the apparatus may be effectively utilized and miniaturization of the mass spectrometer is facilitated.

According to the preferred technical solution, the mass spectrometer further includes an ion source which is arranged between a sample inlet of the vacuum chamber and the linear ion trap.

According to the preferred technical solution, the ion source is one of a photoionization ion source, a dielectric barrier discharge ion source, a glow discharge ion source or an electron bombardment ion source.

The photoionization ion source, the dielectric barrier discharge ion source, the glow discharge ion source, the electron bombardment ion source or other internal ionization sources are integrated in the same vacuum chamber, so as to effectively use space of a single vacuum chamber to complete construction of an entire mass spectrometer system and facilitate miniaturization of the mass spectrometer.

According to the preferred technical solution, a range of the field radius r of the linear ion trap is:

any one or a combination of r≤1 mm, 1 mm≤r≤2 mm, 2 mm≤r≤3 mm, 3 mm≤r≤4 mm and 4 mm≤r≤5 mm.

According to the preferred technical solution, the range of the frequency f of the radio-frequency voltage is:

any one or a combination of 2 MHz≤f≤3 MHz, 3 MHz≤f≤4 MHz, 4 MHz≤f≤5 MHz, 5 MHz≤f≤6 MHz, 6 MHz≤f≤7 MHz, 7 MHz≤f≤8 MHz, 8 MHz≤f≤9 MHz and 9 MHz≤f≤10 MHz.

The present invention provides a mass spectrometry method. The method includes steps: providing a linear ion trap with a field radius r≤5 mm; providing the linear ion trap with a pressure environment of 0.1 Pa≤P≤10 Pa; and providing the linear ion trap with a radio-frequency voltage with a range of a frequency of 2 MHz≤f≤10 MHz.

The present invention further provides a VOC online monitoring device with a mass spectrometer. Since a mass analyzer of the mass spectrometer provided by the present invention may stably operate under a low vacuum condition (for example, 0.1 Pa≤P≤10 Pa), and resolution of mass analysis may still be kept at a relatively high level, for example, a resolution level with a full width at half maximum less than or equal to 1 Th, in a relatively wide range of mass-to-charge ratio, for example, in the range of 20-600 Th or 20-400 Th, the high-resolution mass detection in this range of mass-to-charge ratio may be well adapted to VOC detection. In addition, because the mass spectrometer may be miniaturized conveniently, with a small space occupied, it may be placed in a cabinet of the VOC online monitoring device, which may greatly improve analysis accuracy of the VOC online monitoring device.

The present invention further provides a chromatography-mass spectrometry device with a mass spectrometer. Therefore, the mass spectrometer provided by the present invention may be conveniently miniaturized, so the mass spectrometer may be integrated and combined with a miniaturized chromatographic apparatus, such as a micro-gas chromatography (micro-GC). Accordingly, the mass spectrometer may be matched with an existing miniaturized chromatograph in terms of analysis speed and size, which significantly reduces the size and weight of chromatography-mass spectrometry device, and improves the qualitative and quantitative ability of the mass spectrometer.

DESCRIPTION OF REFERENCE NUMERALS 100, 200—mass spectrometer; 1—sample injection system; 2—ion source; 3—vacuum chamber; 4—linear ion trap, 41—parallel electrodes, 411—slit, 42—end cap electrode; 5—vacuum pump; 6—detector; 7—sample injection interface; 8—power supply; 9—VOC online monitoring device; 91—sampling apparatus, 92—control unit; 10—chromatography-mass spectrometry device; and 11—chromatography device.

DETAILED DESCRIPTION OF THE EMBODIMENTS

Hereinafter, exemplary embodiments will be described in detail with reference to the accompanying drawings. However, the present invention is not limited to the following embodiments, but includes various changes, substitutions and modifications within the technical scope of the present disclosure.

Terms and Explanations

It should be noted that in this specification, the term "roughing pump" refers to a vacuum pump whose ultimate vacuum level is in a pressure range P≥0.1 Pa. According to an operation principle or a structure type, the "roughing pump" may use, including but not limited to, a reciprocating vacuum pump, a rotary-vane vacuum pump, a piston vacuum pump, a dry scroll pump, a diaphragm vacuum pump, a Roots pump, etc.

The term "a VOC online monitoring device" is a monitoring device that is configured on a monitoring point site and used to continuously measure harmful organic gases in a dangerous or industrial environment. "VOC" is an English abbreviation for a volatile organic compound.

Embodiment 1

A mass spectrometer employing a linear ion trap usually has a relatively high demand for vacuum level of vacuum chamber, and particularly, pressure of the vacuum chamber usually needs to be kept at 0.0003 mbar or below. The vacuum level under this vacuum condition is relatively high, in order to achieve this vacuum condition, it is necessary for a pump system to provide a relatively high pumping speed, and accordingly, space occupied by the pump system is also relatively large.

Figure 1:
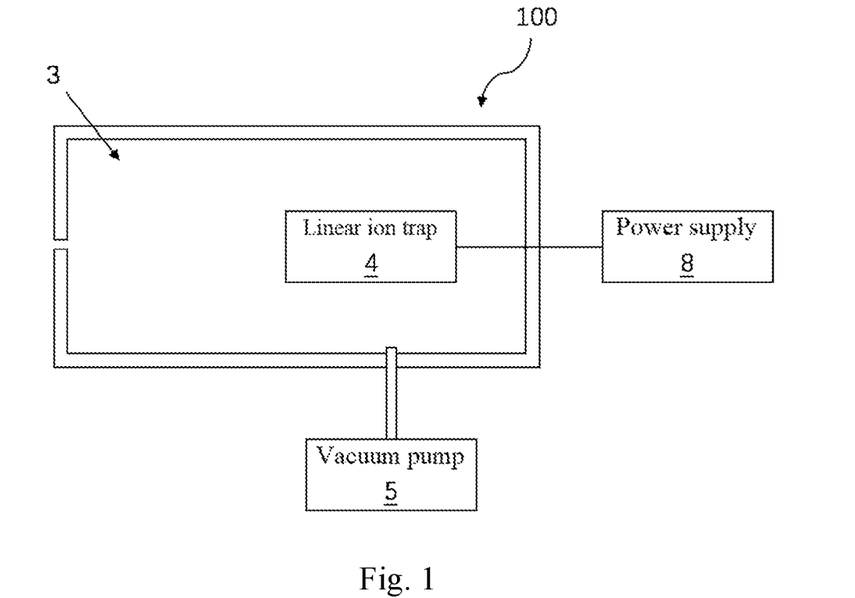
FIG. 1 is a partial structural schematic diagram of a mass spectrometer provided in embodiment 1 of the present invention.

In order to further realize miniaturization of the mass spectrometer, as shown in FIG. 1, some embodiments of the present invention provide a mass spectrometer 100 capable of operating in a low vacuum environment, which includes a vacuum chamber 3 with a range of a working pressure P being 0.1 Pa≤P≤10 Pa, and a linear ion trap 4 arranged in the vacuum chamber 3. The linear ion trap 4 is a hyperboloidal linear ion trap, and is composed of two pairs of hyperbolic poles and two plates at both ends. One pair of the hyperbolic poles are applied with one alternating voltage, and the other one thereof are applied with two alternating voltages. One pole is provided with a slit 411, and ions are driven to be ejected from the slit 411 by changing the three alternating voltages.

In this embodiment, a field radius r of the linear ion trap 4 is r≤5 mm, r being a radius of an inscribed circle of two pairs of parallel electrodes of the linear ion trap 4, and a power supply 8 is configured to provide a radio-frequency voltage for the linear ion trap 4, a frequency f of the radio-frequency voltage being 2 MHz≤f≤10 MHz.

In some embodiments of the present invention, the working pressure P of the vacuum chamber 3 is 0.1 Pa≤P≤10 Pa. As for the reason of such setting, if the working pressure P is higher than 10 Pa, voltages applied to the linear ion trap 4 and detector are relatively high, electrode spacing is small, and accordingly, electric discharge is prone to be caused in such pressure range; and if the working pressure P is less than 0.1 Pa, it is difficult for an existing roughing pump to achieve this vacuum condition. Because the vacuum level under this vacuum condition is relatively low, this vacuum condition may be realized by selecting a roughing pump for evacuating the vacuum chamber 3. Compared with a combined pump unit which is generally selected by a traditional mass spectrometer employing the linear ion trap and is composed of a turbo molecular pump and a roughing pump, the roughing pump has a lower pumping speed, smaller size and lower manufacturing cost. Therefore, the mass spectrometer 100 provided in this embodiment may reduce the total size of a vacuum pump matching the vacuum chamber 3, and further realize miniaturization and a low cost of the mass spectrometer. In addition, compared with multi-stage vacuum chambers, design of a single vacuum chamber has a relatively short ion transmission path and a relatively high ion transmission efficiency, which makes the number of ions available for mass spectrometry relatively large, thus guaranteeing sensitivity of the instrument. In addition, compared with a mass spectrometer provided with multi-stage vacuum chambers and adapted to a plurality of vacuum pumps, the mass spectrometer has a simpler structure, is easy to manufacture and reduces the manufacturing cost.

In the above technical solution, the linear ion trap serving as a mass analyzer is set at 0.1 Pa≤P≤10 Pa, and the mass analyzer is basically the apparatus with the highest requirement for a vacuum performance in the mass spectrometer. Generally speaking, it only requires a minimum pressure required by the mass spectrometer to be in a range of 0.1 Pa≤P≤10 Pa, and then a vacuum level requirement of the mass spectrometer may be met by using a pump with a relatively small size and a relatively low pumping speed, which facilitates miniaturization of the mass spectrometer. Moreover, sensitivity of the linear ion trap working in this pressure range may be improved correspondingly because of better cooling of ions. The efficiencies of ion injection and ejection are improved.

On the other hand, in the process of creating present invention, the inventor found that by limiting the field radius and a voltage frequency of the linear ion trap to the above numerical ranges, the linear ion trap may still obtain a relatively high resolution level even if it works within the pressure range of 0.1 Pa≤P≤10 Pa. For example, it may achieve the resolution level with a full width at half maximum less than or equal to 1 Th in the mass range of 20-600 Th.

If the working pressure P of the vacuum chamber 3 is too low, for example, lower than 0.1 Pa, it will be difficult to achieve a relatively high vacuum level by using a small vacuum pump with a relatively low pumping speed, which is not conducive to miniaturization of the mass spectrometer. If the working pressure of the vacuum chamber is too high, for example, higher than 10 Pa, it is prone to cause electric discharge of the detector and the ion trap.

The frequency f of the radio-frequency voltage should not be too high or too low. When the frequency f is too low, for example, when the frequency f is less than 2 MHz, the resolution and the sensitivity of the mass spectrometer are seriously degraded. However, when the frequency f is too high, for example, when the frequency f is greater than 10 MHz, it is not only more difficult to manufacture the power supply, but also prone to cause electric discharge and sample dissociation.

The field radius r should not be too large. For example, when the field radius r is greater than 5 mm, a voltage with a relatively high frequency is applied to the electrodes of the linear ion trap with an excessively large field radius, which easily leads to electric discharge, and is not conducive to improvement of the resolution.

In this way, the mass spectrometer provided by the present invention may balance various factors such as miniaturization, machining difficulty, resolution, sensitivity and stability, and the mass spectrometer whose mass analyzer may stably operate under a low vacuum condition (for example, 0.1 Pa≤P≤10 Pa), and quality analysis may still be kept at a relatively high level resolution, for example, the full width at half maximum less than or equal to 1 Th, in a relatively wide mass-to-charge ratio range, for example, in the range of 20-600 Th.

In some embodiments, the mass spectrometer further includes a gas supply system communicating with the vacuum chamber 3, which may supply one or more kinds of gases, such as inert gases, into the vacuum chamber 3.

It should be noted that FIG. 1 of this embodiment only shows some necessary structures of the mass spectrometer 100 which may help to achieve the purpose of the present invention. It is easy for those skilled in the art to conceive that the mass spectrometer 100 is further provided with other structures such as an ion source. In this embodiment, types, positions and sizes of other structures such as the ion source are not defined.

Embodiment 2

Figure 2:
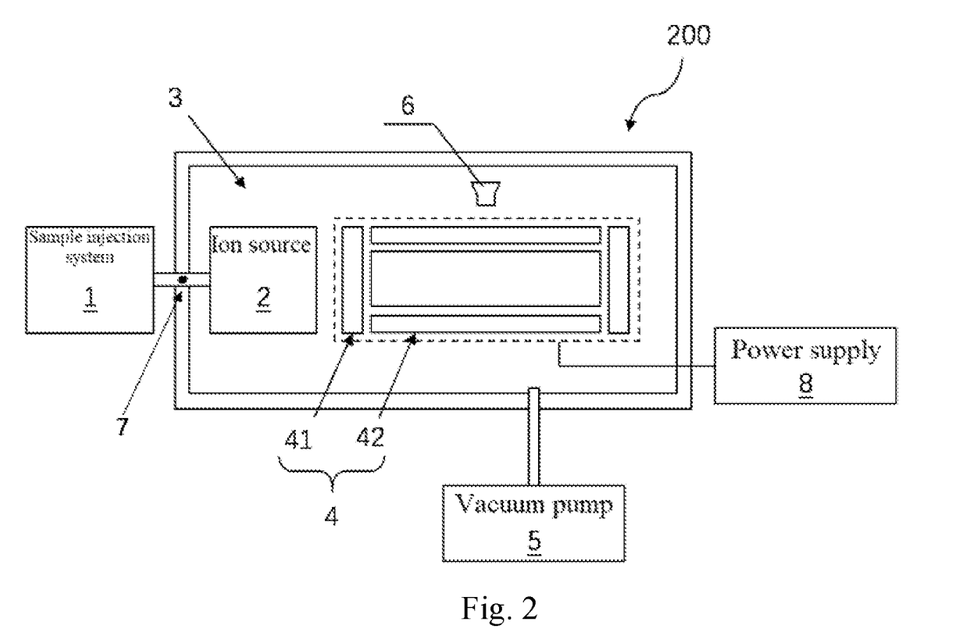
FIG. 2 is a structural schematic diagram of a mass spectrometer provided in embodiment 2 of the present invention.
Figure 3:
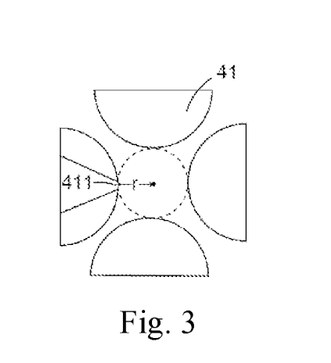
FIG. 3 is a structural schematic diagram of a section view of parallel electrodes of a linear ion trap in FIG. 2.

As shown in FIG. 2 and FIG. 3, a main difference between a mass spectrometer 200 provided in this embodiment and the mass spectrometer 100 provided in embodiment 1 is that the former further includes a sample injection system 1, an ion source 2, a vacuum pump 5 and a detector 6.

The sample injection system 1 is connected to a vacuum chamber 3 through a sample injection interface 7 so as to guide a sample to be analyzed into the vacuum chamber 3. The sample injection system 1 may be a membrane interface connected to the vacuum chamber 3, so as to be suitable for detecting volatile organic compounds. The sample injection interface 7 is one of a conical hole, a cylindrical hole or a capillary, and the capillary may be used for introducing neutral samples or ions. In some technical solutions, the capillary is used as an atmospheric pressure interface. In these technical solutions, an inner diameter of the capillary may be set relatively small, less than 100 μm preferably, such that a low vacuum condition of 0.1 Pa≤P≤10 Pa may be realized by using a small vacuum pump with a relatively low pumping speed. In some other technical solutions, the mass spectrometer may also be used in combination with a chromatograph, for example, the capillary may be configured as a capillary chromatographic column of a gas chromatograph. Hereinafter, the capillary is taken as an example of the sample injection interface 7 for description.

A linear ion trap 4 is arranged in the vacuum chamber 3 and may control the trajectory of an ion beam. The linear ion trap 4 at least includes two pairs of parallel electrodes 41 which are arranged in parallel at intervals, and end cap electrodes 42 which are arranged at both ends, in a length direction, of the parallel electrode 41. The parallel electrodes 41 are evenly distributed relative to a geometric center axis of the linear ion trap 4, and basically extend in the direction of the ion injection. One of the parallel electrodes 41 is provided with a slit 411 for ions to be ejected. Under the action of a specific electric field, the ions may be ejected to the detector 6 in turn according to a mass-to-charge ratio (m/z).

It should be noted that the specific electric field mentioned herein is usually supplied by a radio-frequency voltage to the parallel electrode 41 of the linear ion trap 4 to form a radial bound electric field, supplied by a direct current voltage to the end cap electrode 42 to form an axial bound electric field, and supplied by an excitation alternating current signal to an ion ejection direction (the electrode with slit) to motivate the ions to be ejected.

Preferably, in this embodiment, the ion source 2 is arranged in the vacuum chamber 3, specifically, the ion source 2 is arranged between a sample injection interface of the vacuum chamber 3 and the linear ion trap 4. The ion source 2 may ionize the sample by means of photoionization, dielectric barrier discharge, glow discharge, electron bombardment sources, etc. The ion source 2 is arranged as an internal ionization source, which may make the structure of mass spectrometer more compact, effectively use the space of a single vacuum chamber to complete construction of an entire mass spectrometer system and facilitate miniaturization of the mass spectrometer. In some embodiments, the ion source 2 may also be independently arranged, specifically, the ion source 2 may be connected between the sample injection system 1 and the vacuum chamber 3, for example, an electrospray ion source or an atmospheric pressure chemical ionization source is used. The above embodiments are all within the scope of protection of the present invention. After the sample is ionized by the ion source 2, an ion beam composed of ions with different mass-to-charge ratios (m/z) is formed.

Preferably, the mass spectrometer 100 further includes the membrane interface (not shown in the figure) in communication with the vacuum chamber. The mass spectrometer provided with the membrane interface may be conveniently combined with a VOC detection apparatus. In addition, because a mass spectrometer provided is a miniaturized mass spectrometer, which may be integrated in the VOC detection apparatus, for example, inside a case of an online monitoring device, so as to improve accuracy of VOC detection.

The detector 6 is arranged at an ion outlet of the linear ion trap 4, and an ion signal with relatively high resolution may be collected by arranging the detector 6 near the ion outlet of the linear ion trap 4. Therefore, by integrating the linear ion trap 4 and the detector 6 in the same vacuum chamber, internal space of the apparatus may be effectively utilized and miniaturization of the mass spectrometer is facilitated. Specifically, the detector 6 directly faces the position of slit 411. Specifically, the detector 6 may be, for example, a microchannel plate detector, an electron multiplier detector, or a Faraday cup.

Preferably, the detector 6 further includes a recorder (not shown in the figure), which may display a result of mass spectrometry in the form of graphs, data or a combination thereof.

The power supply 8 may provide the specific electric field for the linear ion trap 4, and specifically, the power supply 8 may at least provide a radio-frequency voltage for the linear ion trap 4.

The vacuum pump 5 is connected to the vacuum chamber 3 and may provide a low-pressure environment for the vacuum chamber 3. Selection of vacuum pump 5 is related to vacuum conditions required by the corresponding vacuum chamber 3. In this embodiment, a working pressure P of the vacuum chamber 3 is $0.1\ Pa \leq P \leq 10\ Pa$. Because a vacuum level of this vacuum condition is relatively low, the vacuum pump 5 may realize this vacuum condition by selecting a roughing pump. Specifically, the vacuum pump 5 may be a roughing pump with a range of pumping speed S being $S \leq 100$ L/min, such as a reciprocating vacuum pump, a rotary-vane vacuum pump, a piston vacuum pump, a dry scroll pump, a diaphragm vacuum pump, and a Roots pump. Compared with a combined pump unit which is generally selected by a traditional mass spectrometer using the linear ion trap and is composed of a turbo molecular pump and a roughing pump, the above roughing pump of each type has a lower pumping speed, smaller size and lower manufacturing cost. Therefore, the mass spectrometer 200 provided in this embodiment may have a reduced total size of the vacuum pump 5, and further miniaturization and a low cost of the mass spectrometer are realized.

Considering that an analytical performance of the mass spectrometer 200 may be affected under the low vacuum condition, in this embodiment, the analytical performance of the mass spectrometer 200 provided in this embodiment is mainly considered and discussed from the resolution of mass spectrometry.

The radio-frequency voltage applied by the power supply 8 to the linear ion trap 4 is $V \cos \omega t$, the radio-frequency voltage has an amplitude value of V and a frequency f ($f = \omega/2\pi$), the shortest distance between each electrode and the geometric center axis of the linear ion trap 4 (a radius of an inscribed circle of two pairs of parallel electrodes 41) is called the field radius r of the linear ion trap 4, and according to an empirical equation: $m/\Delta m \propto \omega/P$, the resolution $m/\Delta m$ of the linear ion trap decreases along with increase of the working pressure P. In order to improve the resolution, it is necessary to increase an oscillation frequency $\omega$, that is, to increase the radio frequency f. According to the Mathieu equation: $q = 4\ eV/m\omega^2 r^2$ (wherein e is a charge of an ion and m is a mass of the ion), when an ion ejection condition q is constant, the higher of the radio frequency f, the higher of the amplitude value V of the radio-frequency voltage. Since the excessively high amplitude value V of the radio-frequency voltage will lead to the electric discharge phenomenon, in order to avoid electric discharge, the amplitude value V of the radio-frequency voltage should not be too high. Therefore, under the condition of guaranteeing the relatively high radio frequency f, it is necessary to reduce the field radius r accordingly.

Hereinafter, influence of the field radius r of the linear ion trap 4 and the frequency f of the radio-frequency voltage applied to the linear ion trap 4 on the analytical performance of the mass spectrometer 200 will be described. According to the Mathieu equation, when the radio frequency f is too high, the amplitude value V of the applied radio-frequency voltage needs to be correspondingly increased, which will lead to an increase in the risk of electric discharge. On the other hand, if the frequency f is too high, it may cause ion dissociation and affect the quality of a spectrum. In order to reduce the risk of electric discharge, the field radius r of an ion trap may be appropriately reduced to reduce the required radio-frequency voltage V. However, if the field radius r is too small, the parallel electrode 41 will be difficult for fabrication. In addition, the electric discharge phenomenon is prone to occur when electrode spacing is too small. The field radius r also limits the ion capacity of the linear ion trap 4 when being too small. Therefore, it is necessary to properly select values of the radio frequency f and the field radius r, such that the mass spectrometer may keep good analytical performance.

Specifically, based on the above considerations, in this embodiment, the range of the field radius r of the linear ion trap 4 is designed to be r≤5 mm, and the range of the frequency f of the radio-frequency voltage applied to the linear ion trap 4 is designed to be 2 MHz≤f≤10 MHz.

Further, the range of the field radius r of the linear ion trap 4 is:

any one or a combination of r≤1 mm, 1 mm≤r≤2 mm, 2 mm≤r≤3 mm, 3 mm≤r≤4 mm and 4 mm≤r≤5 mm.

Further, the range of the frequency f of the radio-frequency voltage is:

any one or a combination of 2 MHz≤f≤3 MHz, 3 MHz≤f≤4 MHz, 4 MHz≤f≤5 MHz, 5 MHz≤f≤6 MHz, 6 MHz≤f≤7 MHz, 7 MHz≤f≤8 MHz, 8 MHz≤f≤9 MHz and 9 MHz≤f≤10 MHz.

It should be noted that when the radio frequency f exceeds a specific value, such as 5 MHz or 6 MHz, and currently, it is difficult to manufacture the power supply and power consumption of the power supply is high. Moreover, under the condition of very high frequency, ion dissociation is serious, and noise is increased to cause a space charge effect, which degrades the resolution and quality of the mass spectrum. Therefore, further preferably, the range of the frequency of the radio-frequency voltage is 2 MHz≤f≤5 MHz or 2 MHz≤f≤6 MHz, and further preferably, the range of the frequency of the radio-frequency voltage is 3 MHz≤f≤6 MHz or 4 MHz≤f≤6 MHz or 4 MHz≤f≤5 MHz.

In the mass spectrometer 200 provided in this embodiment, the range of the field radius r and the range of the frequency f of the radio-frequency voltage of the linear ion trap 4 are designed, such that miniaturization of the instrument is achieved while the mass spectrometer 200 guarantees good resolution.

Preferably, this embodiment provides a mass spectrometry method. The method includes steps: providing a linear ion trap with a field radius r≤5 mm; providing the linear ion trap with a pressure environment of 0.1 Pa≤P≤10 Pa; and providing the linear ion trap with a radio-frequency voltage with a range of frequency of 2 MHz≤f≤10 MHz.

Embodiment 3

This embodiment provides a detection system. Specifically, the detection system is a VOC online monitoring device 9 or a chromatography-mass spectrometry device 10. More specifically, both the VOC online monitoring device and the chromatography-mass spectrometry device may employ the mass spectrometer provided in embodiment 1 or embodiment 2. Hereinafter, the VOC online monitoring device 9 and the chromatography-mass spectrometry device 10 both employ the mass spectrometer 200 provided in embodiment 2 for example.

Figure 4:
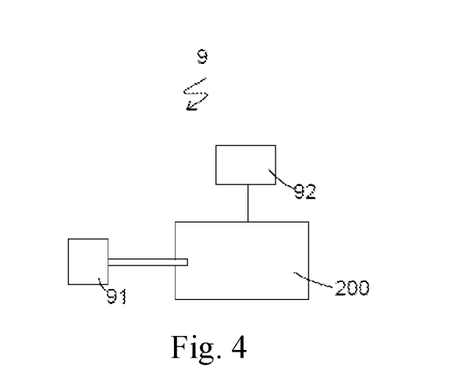
FIG. 4 is a structural schematic diagram of a VOC online monitoring device provided in embodiment 3 of the present invention.

As shown in FIG. 4, the VOC online monitoring device 9 further includes a sampling device 91 connected to the mass spectrometer 200 and a control unit 92 for controlling operation of the VOC online monitoring device 9.

Since a mass analyzer (a linear ion trap 4) of the mass spectrometer 200 may stably operate under a low vacuum condition (for example, 0.1 Pa≤P≤10 Pa), and resolution of mass analysis may still be kept at a relatively high level, for example, a resolution level with a full width at half maximum less than or equal to 1 Th, in a relatively wide range of mass-to-charge ratio, for example, in the range of 20-600 Th, and the high-resolution mass detection in this range of mass-to-charge ratio may be well adapted for VOC detection. In addition, because the mass spectrometer may be miniaturized conveniently, with a small space occupied, it may be placed in a cabinet of the VOC online monitoring device, which may greatly improve analysis accuracy of the VOC online monitoring device.

Figure 5:
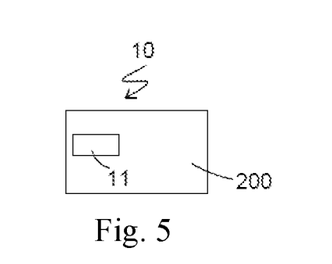
FIG. 5 is a schematic structural diagram of a chromatography-mass spectrometry device provided in embodiment 3 of the present invention.

As shown in FIG. 5, when the mass spectrometer 200 is applied to the chromatography-mass spectrometry device 10, the mass spectrometer 200 may be conveniently miniaturized, so the mass spectrometer may be integrated and combined with a miniaturized chromatographic apparatus 11, such as a micro-gas chromatography (micro-GC). Specifically, the micro-gas chromatography may be integrated inside the mass spectrometer 200, which further miniaturizes the chromatography-mass spectrometry device 10. Therefore, the mass spectrometer 200 may match an existing miniaturized chromatographic device in terms of analysis speed and size, which significantly reduces the size and weight of the chromatography-mass spectrometry device. In addition, the qualitative and quantitative ability of the mass spectrometer 200 are greatly enhanced when it is combined with the chromatographic device.

Experimental Analysis

FIGS. 6-12 show resolution in a range of 20-600 Th of a mass spectrometer 100 in embodiment 1 of the present invention, namely a measurement or simulation result of full width at half maximum (FWHM).

Figure 6:
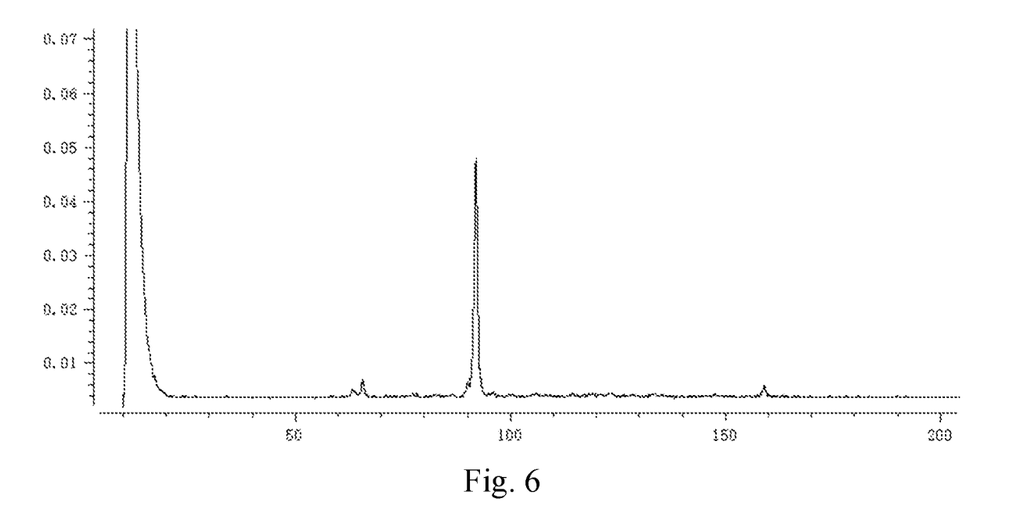
FIG. 6 is a mass spectrum of toluene obtained at pressure of P=8.5 Pa by using a linear ion trap with a field radius r=1 mm, and a radio frequency f=4.14 MHz.
Figure 7:
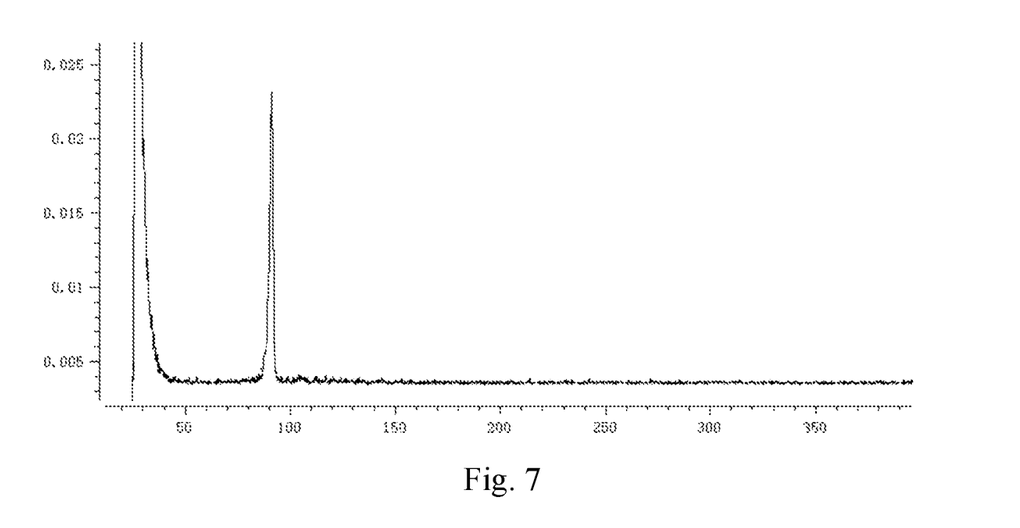
FIG. 7 is a mass spectrum of toluene obtained at pressure of P=8.5 Pa by using a linear ion trap with a field radius r=1 mm, and a radio frequency f=1.79 MHz.
Figure 8:
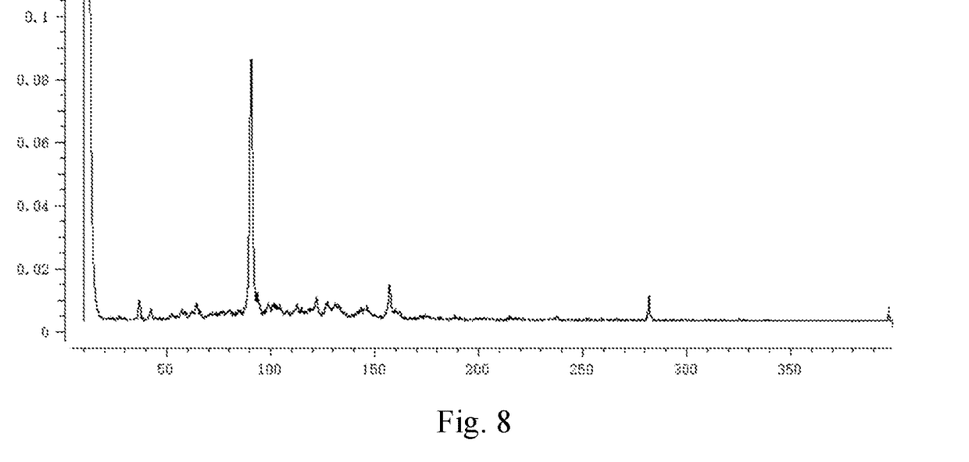
FIG. 8 is a mass spectrum of toluene obtained at pressure of P=8.3 Pa by using a linear ion trap with a field radius r=1 mm, and a radio frequency f=5.8 MHz.

FIGS. 6-8 are mass spectra obtained by using a linear ion trap with a field radius of 1 mm to measure toluene with a concentration of 10 ppm.

It may be seen from FIG. 6 that under the conditions of a field radius r=1 mm, a working pressure P=8.5 Pa and a radio frequency f=4.14 MHz, a full width at half maximum FWHM=0.9 Th, and resolution is relatively high.

It may be seen from FIG. 7 that under the condition that other parameters such as the field radius and the working pressure are controlled to be basically the same, the radio frequency is set at f=1.79 MHz, and the full width at half maximum is accordingly changed to FWHM=1.8 Th.

It may be seen from FIG. 8 that under the conditions of the field radius r=1 mm, the working pressure P=8.3 Pa, the radio frequency f=5.8 MHz, the full width at half maximum FWHM=1.5 Th, and the noise is generated, that is, when the frequency rises, ions are prone to dissociation, which affects the quality of the spectrum.

It may be seen from experimental results of FIGS. 6-8, a set value of the frequency should not be too high or too low. If the frequency is set too high, the ions are prone to generate noise due to dissociation, which affects the quality of the spectrum. If the frequency is set too low, the resolution and sensitivity of the mass spectrometer may be decreased to some extent. On the basis of the above factors, when the field radius is configured to be 1-2 mm, and the working pressure is configured to be 8-10 Pa, the radio frequency is preferably configured to be in the range of 3-5 MHz, and more preferably in the range of 3.5-4.5 MHz, the resolution and sensitivity of the mass spectrometer are improved, and resolution reaches the level that the full width at half maximum is less than or equal to 1 Th in mass range of 20-600 Th.

FIGS. 9-12 are resolution data of spectra of reserpine obtained by simulating linear ion traps with different structures and working conditions, with peak appearance at 609-611 Th.

Figure 9:
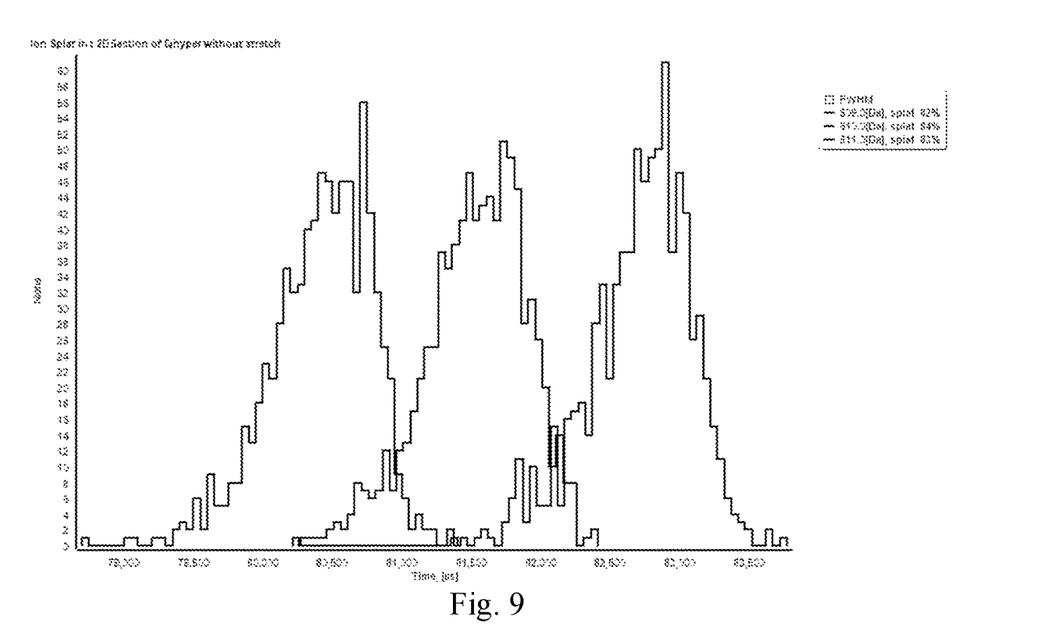
FIG. 9 is simulation data using a linear ion trap with a field radius r=0.5 mm, a working pressure P=2 Pa and a radio frequency f=9 MHz to perform mass spectrum of reserpine, with peak appearance at 609-611 Th.

FIG. 9 shows resolution data of a mass spectrometry peak in a range of 609-611 Th, obtained under the conditions of a working pressure P=2 Pa, a field radius r=0.5 mm, a radio frequency f=9 MHz and a scanning speed of 850 Th/s, a range of the full width at half maximum FWHM of the mass spectrometry peak in the figure being 0.67 Th≤FWHM≤0.75 Th.

Figure 10:
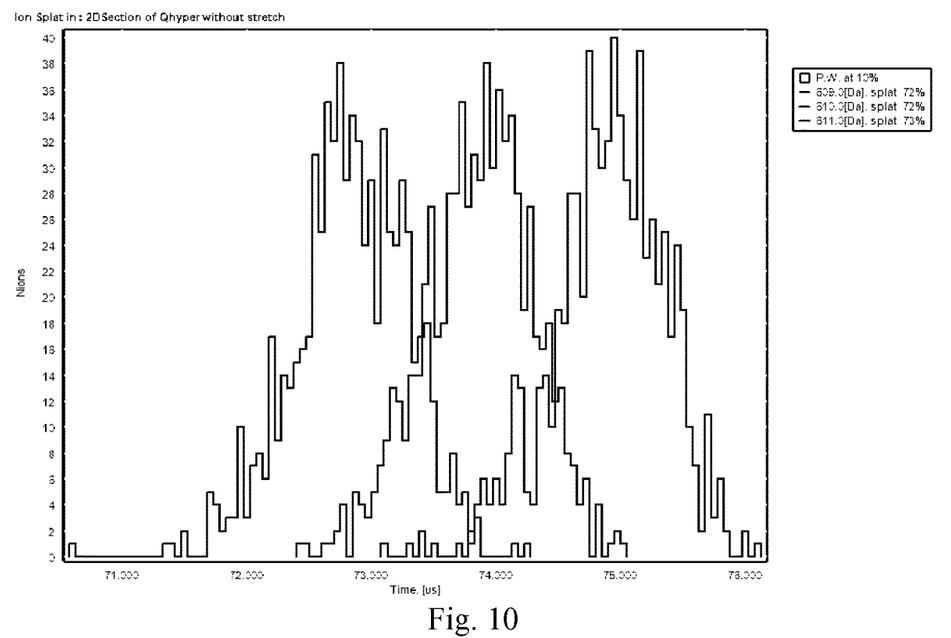
FIG. 10 is simulation data using a linear ion trap with a field radius r=1 mm, a working pressure P=2 Pa and a radio frequency f=6 MHz to perform mass spectrum of reserpine, with peak appearance at 609-611 Th.

FIG. 10 shows resolution data of a mass spectrometry peak in a range of 609-611 Th, obtained under the conditions of a working pressure P=2 Pa, a field radius r=1 mm, a radio frequency f=6 MHz and a scanning speed of 900 Th/s, a range of the full width at half maximum FWHM of the mass spectrometry peak in the figure being 0.8 Th≤FWHM≤0.89 Th.

It may be seen from this that the resolution is better under the condition that the field radius r=0.5 mm than the condition that the field radius r=1 mm. However, on one hand, as the field radius decreases, a manufacturing cost will be gradually increased, and on the other hand, the field radius also limits the ion capacity of the linear ion trap 4 when being too small. Therefore, preferably, the field radius r has a lower limit, which may be selected from the following values: 0.1 mm, 0.2 mm, 0.3 mm, 0.4 mm, 0.5 mm, 0.6 mm, 0.7 mm, 0.8 mm or 0.9 mm.

Figure 11:
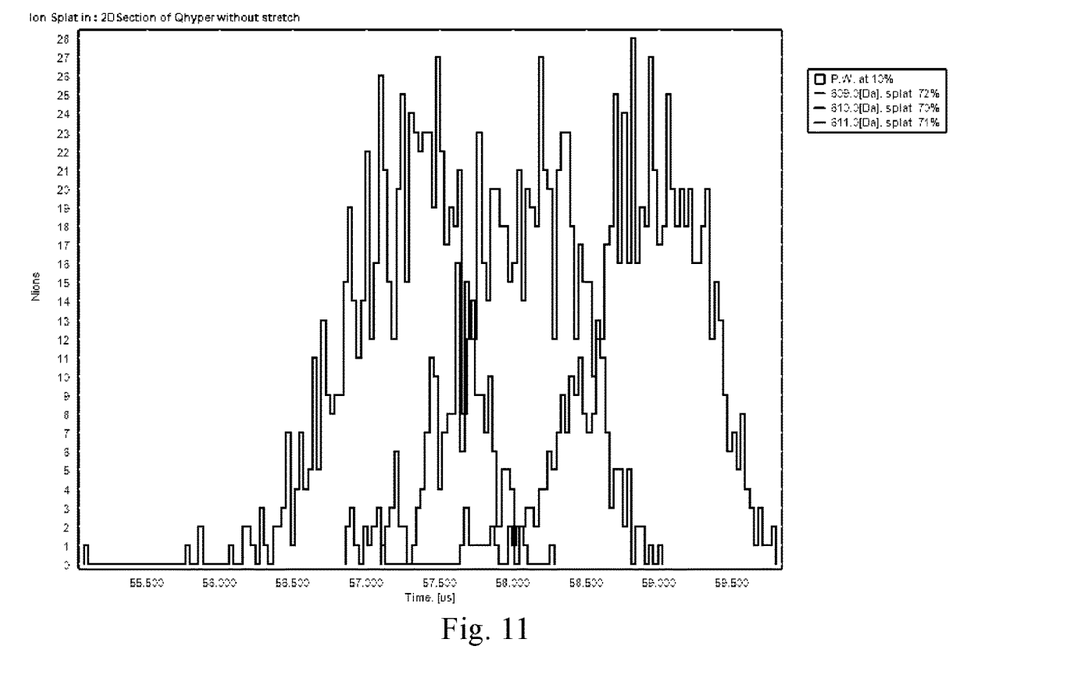
FIG. 11 is simulation data using a linear ion trap with a field radius r=1 mm, a working pressure P=2 Pa and a radio frequency f=5.4 MHz to perform mass spectrum of reserpine, with peak appearance at 609-611 Th.

FIG. 11 shows that a range of full width at half maximum FWHM is 0.96 Th≤FWHM≤1.13 Th under the conditions of a working pressure P=2 Pa, a field radius r=1 mm, a radio frequency f=5.4 MHz and a scanning speed of 1,200 th/s.

Figure 12:
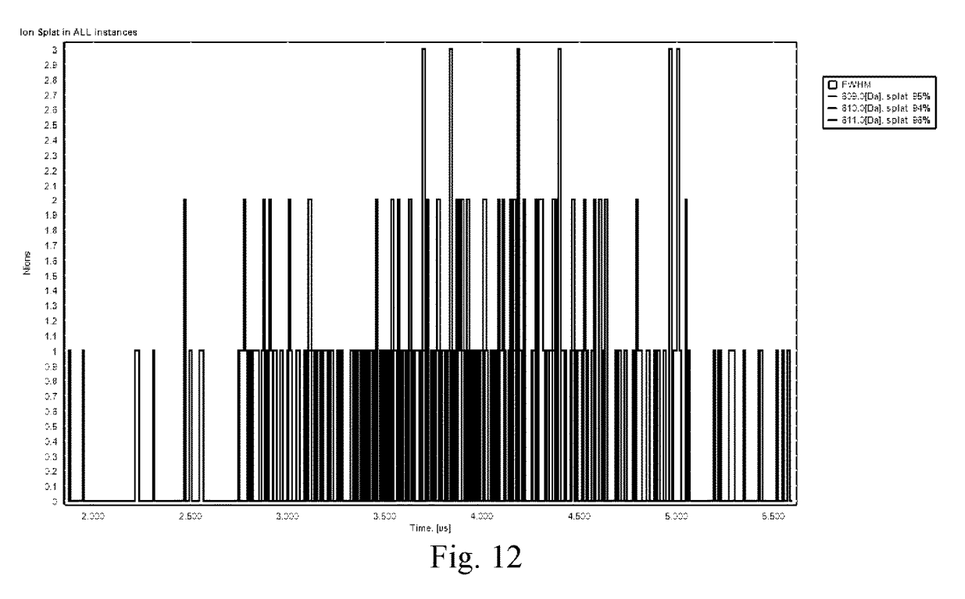
FIG. 12 is simulation data using a linear ion trap with a field radius r=2 mm, a working pressure P=2 Pa and a radio frequency f=4.2 MHz to perform mass spectrum of reserpine, with peak appearance at 609-611 Th.

FIG. 12 shows that a range of full width at half maximum FWHM is FWHM>1 Th under the conditions of a working pressure P=2 Pa, a field radius r=2 mm, a radio frequency f=4.2 MHz and a scanning speed of 2,000 Th/s.

It may be seen from FIG. 12 that the field radius r should not be too high, otherwise it will easily lead to electric discharge, and the resolution may not meet the requirements. Therefore, the field radius r has an upper limit, for example, the field radius r should be less than or equal to 5 mm. Preferably, the field radius is r≤4 mm, r≤3 mm or ≤2 mm.

In some embodiments of the present invention, influence of the working pressure on the resolution under the specified field radius and radio frequency is further studied. At the scanning speed of 10,000 Th/s, a linear ion trap with a field radius r=1 mm and a radio frequency f=6 MHz is used to simulate the influence of the working pressure P on the full width at half maximum by adjusting the working pressure.

The simulation result shows that the full width at half maximum is FWHM=1 Th when the working pressure P=5 Pa, and the full width at half maximum is FWHM=1.5 Th when the working pressure P=10 Pa. It may be seen from the above results that when the field radius r and radio frequency f are kept constant, the full width at half maximum increases with increase of the working pressure P. Therefore, the working pressure P should neither be too high nor too low. In the embodiment of the present invention, the appropriate working pressure P may be reasonably selected in the range of 0.1 Pa≤P≤10 Pa according to the actual situation, so as to balance miniaturization of a pump system, the electric discharge problems of the detector and the ion trap, and the resolution.

Those of ordinary skill in the art may understand that in each embodiment described above, many technical details have been put forward in order to make readers better understand the present application. However, even without these technical details and various changes and modifications based on the above embodiments, technical solutions to be protected as required in the claims of the present application may be basically realized. Therefore, in a practical application, various changes can be made to the above embodiment in form and detail without departing from the spirit and scope of the present invention.

What is claimed is:

1. A mass spectrometer, comprising:
a vacuum chamber, a range of a working pressure P of the vacuum chamber being 0.1 Pa≤P≤10 Pa;
a linear ion trap, arranged in the vacuum chamber, wherein a range of a field radius r of the linear ion trap is r≤5 mm;
a detector, arranged in the vacuum chamber; and
a power supply, configured to provide a radio-frequency voltage for the linear ion trap, a range of a frequency f of the radio-frequency voltage being 2 MHz≤f≤10 MHz.

2. The mass spectrometer according to claim 1, further comprising:
a vacuum pump, connected to the vacuum chamber, wherein the vacuum pump is a reciprocating vacuum pump, a rotary-vane vacuum pump, a piston vacuum pump, a dry scroll pump, a diaphragm vacuum pump or a Roots pump.

3. The mass spectrometer according to claim 2, wherein a range of a pumping speed S of the vacuum pump is S≤100 L/min.

4. The mass spectrometer according to claim 1, further comprising:
a capillary, configured to guide a sample into the vacuum chamber.

5. The mass spectrometer according to claim 1, further comprising a membrane injection interface communicating with the vacuum chamber.

6. The mass spectrometer according to claim 1, further comprising:
an ion source arranged between a sample inlet of the vacuum chamber and the linear ion trap.

7. The mass spectrometer according to claim 6, wherein the ion source is one or a combination of a photoionization ion source, a dielectric barrier discharge ion source, a glow discharge ion source or an electron bombardment ion source.

8. The mass spectrometer according to claim 1, wherein the range of the field radius r of the linear ion trap is:
any one or a combination of r≤1 mm, 1 mm≤r≤2 mm, 2 mm≤r≤3 mm, 3 mm≤r≤4 mm and 4 mm≤r≤5 mm.

9. The mass spectrometer according to claim 1, wherein the range of the frequency f of the radio-frequency voltage is:
any one or a combination of 2 MHz≤f≤3 MHz, 3 MHz≤f≤4 MHz, 4 MHz≤f≤5 MHz, 5 MHz≤f≤6 MHz, 6 MHz≤f≤7 MHz, 7 MHz≤f≤8 MHz, 8 MHz≤f≤9 MHz and 9 MHz≤f≤10 MHz.

10. A mass spectrometry method, comprising following steps:
providing a vacuum chamber, a range of a working pressure P of the vacuum chamber being 0.1 Pa≤P≤10 Pa;
providing a linear ion trap with a field radius r≤5 mm in the vacuum chamber;
providing a detector in the vacuum chamber; and
providing the linear ion trap with a radio-frequency voltage with a frequency of 2 MHz≤f≤10 MHz.

11. A VOC online monitoring apparatus, the VOC online monitoring apparatus being provided with the mass spectrometer according to claim 1.

12. A gas chromatography-mass spectrometry apparatus, the gas chromatography-mass spectrometry apparatus being provided with the mass spectrometer according to claim 1.

\* \* \* \* \*